United States Patent
Nagai et al.

(10) Patent No.: US 8,206,663 B2
(45) Date of Patent: Jun. 26, 2012

(54) AGITATING DEVICE

(75) Inventors: Takaaki Nagai, Kobe (JP); Mitsuo Yamasaki, Kobe (JP)

(73) Assignee: Sysmex Corporation, Kobe (JP)

( * ) Notice: Subject to any disclaimer, the term of this patent is extended or adjusted under 35 U.S.C. 154(b) by 0 days.

(21) Appl. No.: 12/974,999

(22) Filed: Dec. 21, 2010

(65) Prior Publication Data

US 2011/0116971 A1 May 19, 2011

Related U.S. Application Data

(63) Continuation of application No. 11/599,842, filed on Nov. 15, 2006, now Pat. No. 7,879,292.

(30) Foreign Application Priority Data

Nov. 15, 2005 (JP) ................................. 2005-330498

(51) Int. Cl.
 *B01L 3/00* (2006.01)
(52) U.S. Cl. .......... 422/500; 422/50; 422/509; 422/547; 436/180
(58) Field of Classification Search .............. 422/63–65, 422/50, 500, 509, 247; 436/180
See application file for complete search history.

(56) References Cited

U.S. PATENT DOCUMENTS

2002/0021983 A1 * 2/2002 Comte et al. .................... 422/65

FOREIGN PATENT DOCUMENTS

JP 63-187158 8/1988

OTHER PUBLICATIONS

Office Action from counterpart Chinese Application No. 200610138139.8, dated Apr. 27, 2010, 5 pages.

* cited by examiner

*Primary Examiner* — Jyoti Nagpaul
(74) *Attorney, Agent, or Firm* — Brinks Hofer Gilson & Lione

(57) ABSTRACT

An agitating device for agitating a blood sample in a sample container is disclosed. The agitating device includes a base comprising a horizontally-supported shaft, a container holder including a first hand and a second hand, the first hand having a first hole at one end and a first hold portion at other end, the second hand having a second hole at one end and a second hold portion at other end, the first and second holes through which the shaft is inserted, the first and second hands being rotatable relative to the shaft and the first and second hold portions faced each other, and an agitation drive unit including a contact member for contacting the container holder and a drive source for reciprocating the contact member contacting the container holder between a lower position and an upper position.

20 Claims, 15 Drawing Sheets

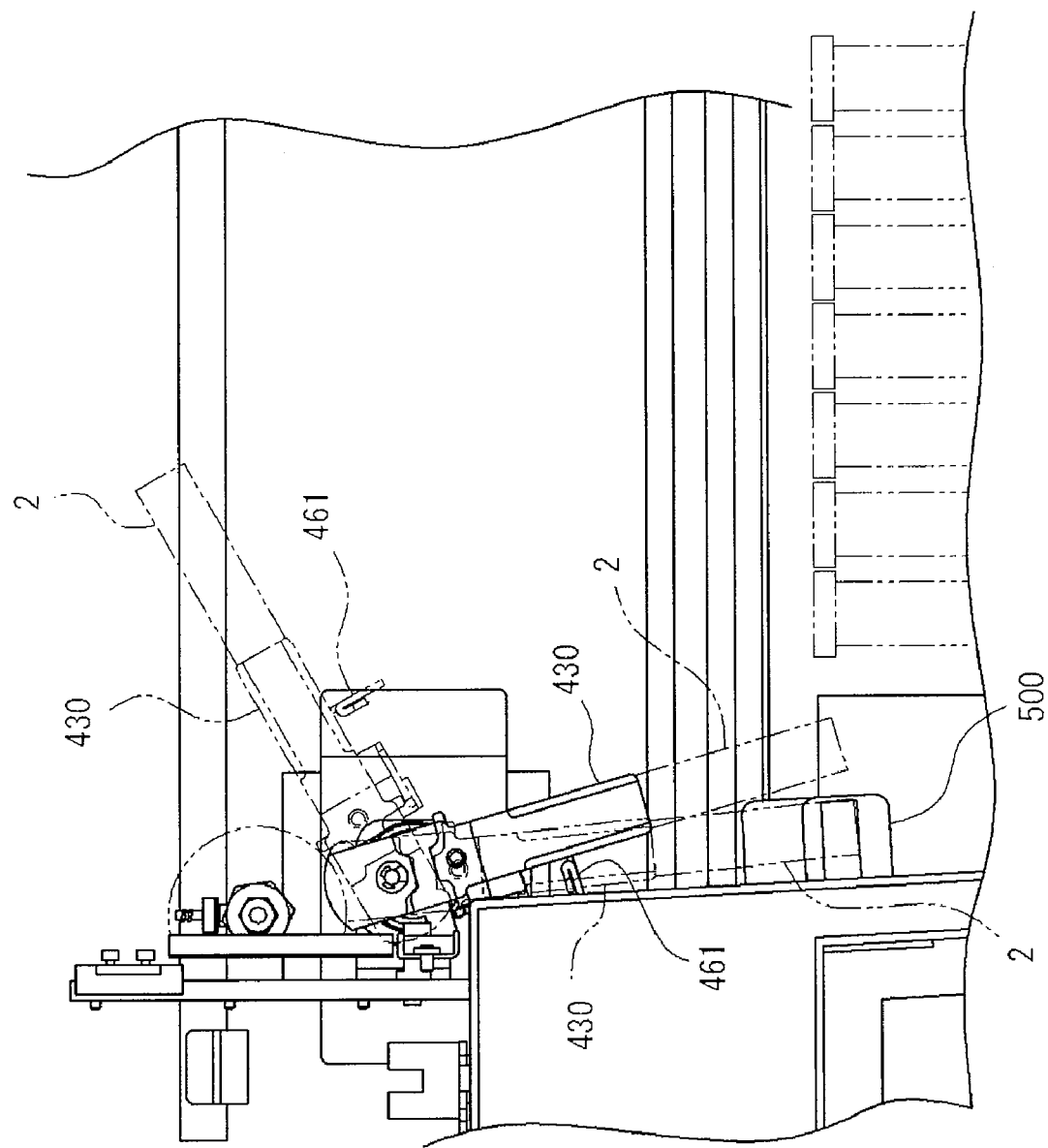

AGITATING DEVICE

This patent document is a continuation of U.S. patent application Ser. No. 11/599,842, filed on Nov. 15, 2006 now U.S. Pat. No. 7,879,292, which claims priority to to Japanese Patent Application No. JP2005-330498 filed Nov. 15, 2005, all of which are hereby incorporated by reference in their entireties.

TECHNICAL FIELD

The present disclosure relates to an agitating device.

BACKGROUND

Sample analyzers include, for example, blood analyzers. Such sample analyzers aspirate a sample such as blood or the like collected in a sample container (collection tube), mix the aspirated sample with reagent, measure the mixed sample and analyse the measured sample to obtain analysis results.

The sample analyser comprises an agitating device that is used mix the sample in the sample container before the sample is aspirated by the sample analyzer.

For example, the sample agitating and aspirating device disclosed in Japanese Laid-Open Patent Publication No. 63-187158. This sample agitating and aspirating device grips a sample container held in a rack by means of hand, and repeats a reciprocating rotation movement of the hand gripping the sample container by a rotation drive cylinder. Thus, the sample within the sample container is vigorously agitated.

The hand is provided so as to be movable relative to the support member that is base of the sample agitating and aspirating device, and the hand removes the sample container from the rack and agitates the sample container.

The rotation drive cylinder that provides the rotational drive to agitate the hand is provided integratedly with the hand, and configured so as to move together with the hand within the device.

Therefore, a large drive force is required to move the hand via the rotation drive cylinder used for agitation. A large drive source is needed to obtain such a large drive force, thus enlarging the size of the apparatus.

SUMMARY

The scope of the present invention is defined solely by the appended claims, and is not affected to any degree by the statements within this summary.

In one embodiment, an agitating device for agitating a blood sample in a sample container is disclosed. The agitating device includes a base comprising a horizontally-supported shaft, a container holder including a first hand and a second hand, the first hand having a first hole at one end and a first hold portion at other end, the second hand having a second hole at one end and a second hold portion at other end, the first and second holes through which the shaft is inserted, the first and second hands being rotatable relative to the shaft and the first and second hold portions faced each other, and an agitation drive unit including a contact member for contacting the container holder and a drive source for reciprocating the contact member contacting the container holder between a lower position and an upper position.

In another embodiment, a blood sample analyzer for analyzing a blood sample in a sample container is disclosed. The blood sample analyzer includes a base comprising a horizontally-supported shaft, a container holder comprising first hand and second hand, the first hand including a first hole at one end and a first hold portion at other end, the second hand including a second hole at one end and a second hold portion at other end, the first and second holes through which the shaft is inserted, the first and second hands being rotatable relative to the shaft and the first and second hold portions faced each other, an agitation drive unit comprising a contact member for contacting the container holder and a drive source for reciprocating the contact member contacting the container holder between a lower position and an upper position, an aspirator comprising an aspiration tube and aspirating a blood sample contained in the agitated sample container, a measurement sample preparer comprising a chamber for preparing a measurement sample by mixing the aspirated blood sample and a reagent, and a measurement part measuring blood cells contained in the measurement sample.

BRIEF DESCRIPTION OF THE DRAWINGS

FIG. 15 is a side view showing the container holder agitation operation;

DETAILED DESCRIPTION OF THE PREFERRED EMBODIMENT

The preferred embodiments of the present invention are described hereinafter.

Figure 1:
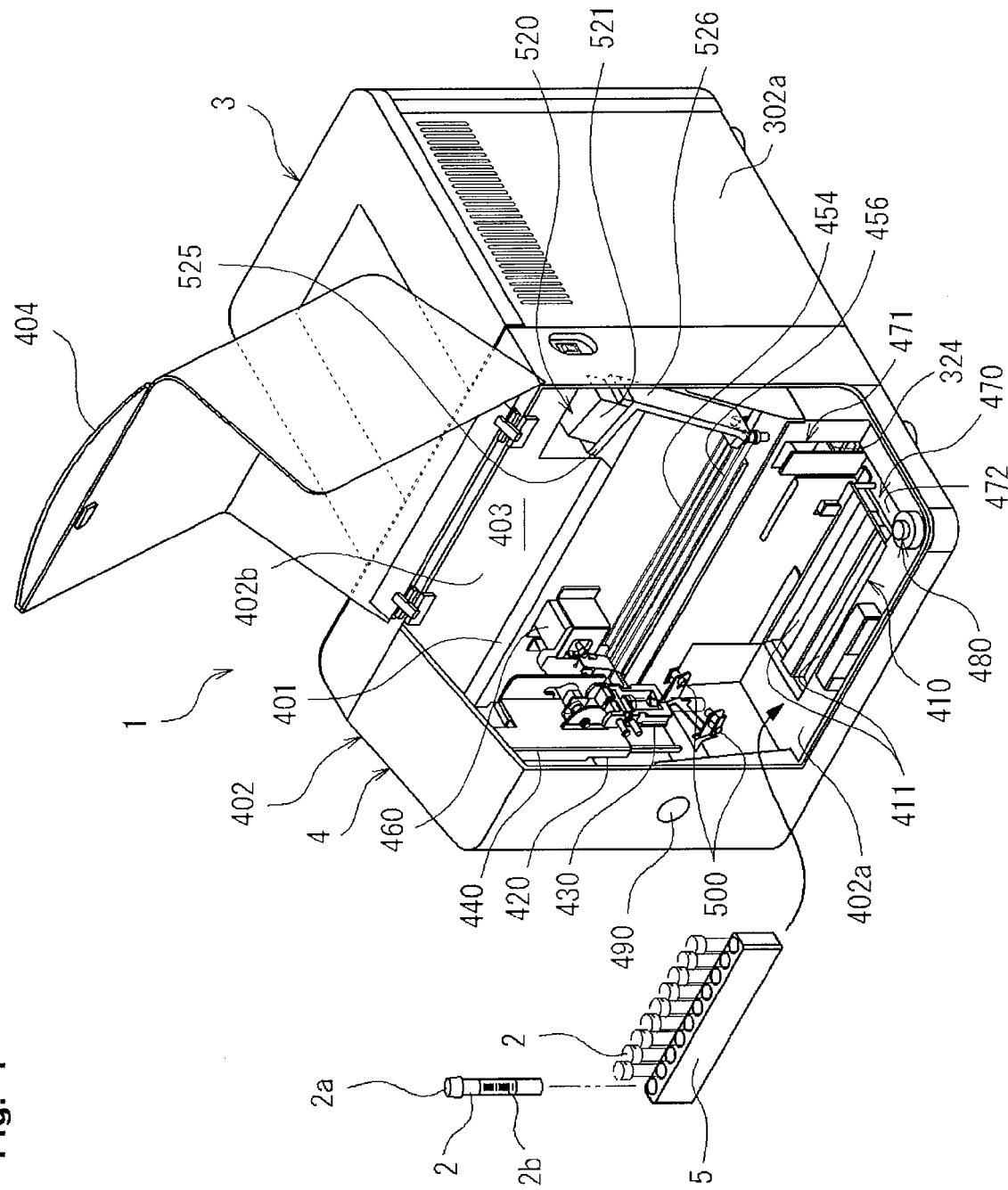
FIG. 1 is a perspective view of a sample analyzer.

FIG. 1 shows a blood analyzer as an example of a sample analyzer 1. The sample analyzer 1 measures a blood sample contained in a sample container (collection tube) 2, and the measurement result is analyzed by a computer 7 (omitted from FIG. 1).

The sample analyzer 1 is provided with a sample analyzer main body apparatus (blood analyzer main body apparatus) 3 with the function of measuring the sample blood, and a sample container supplier (sampler) 4 that automatically supplies a plurality of sample containers to the sample analyzer main body 3.

Figure 2:
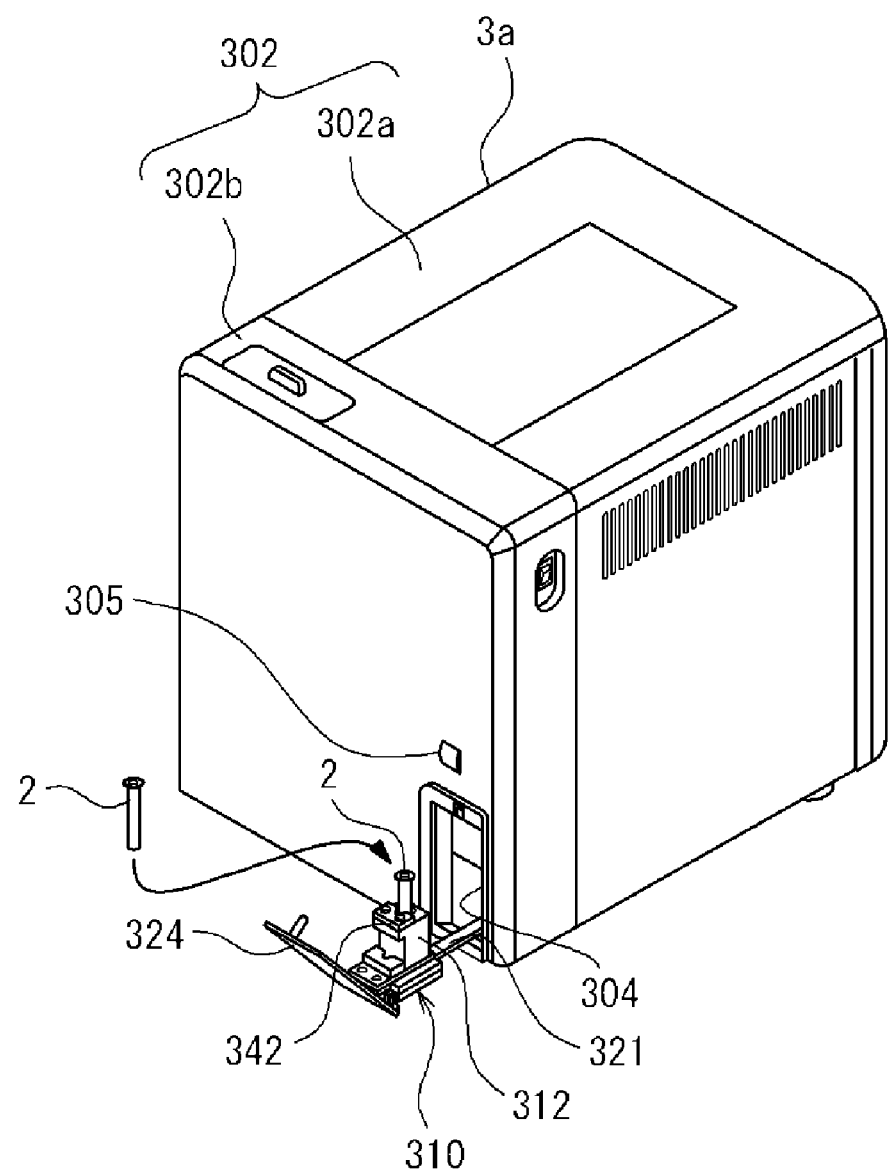
FIG. 2 is a perspective view of a manual placement-type sample analyzer (sample analyzer main body)

As shown in FIG. 2, the sample analyzer main body 3 is originally configured as a manual placement-type sample analyzer 3a that measures a manually placed sample container 2.

Figure 3:
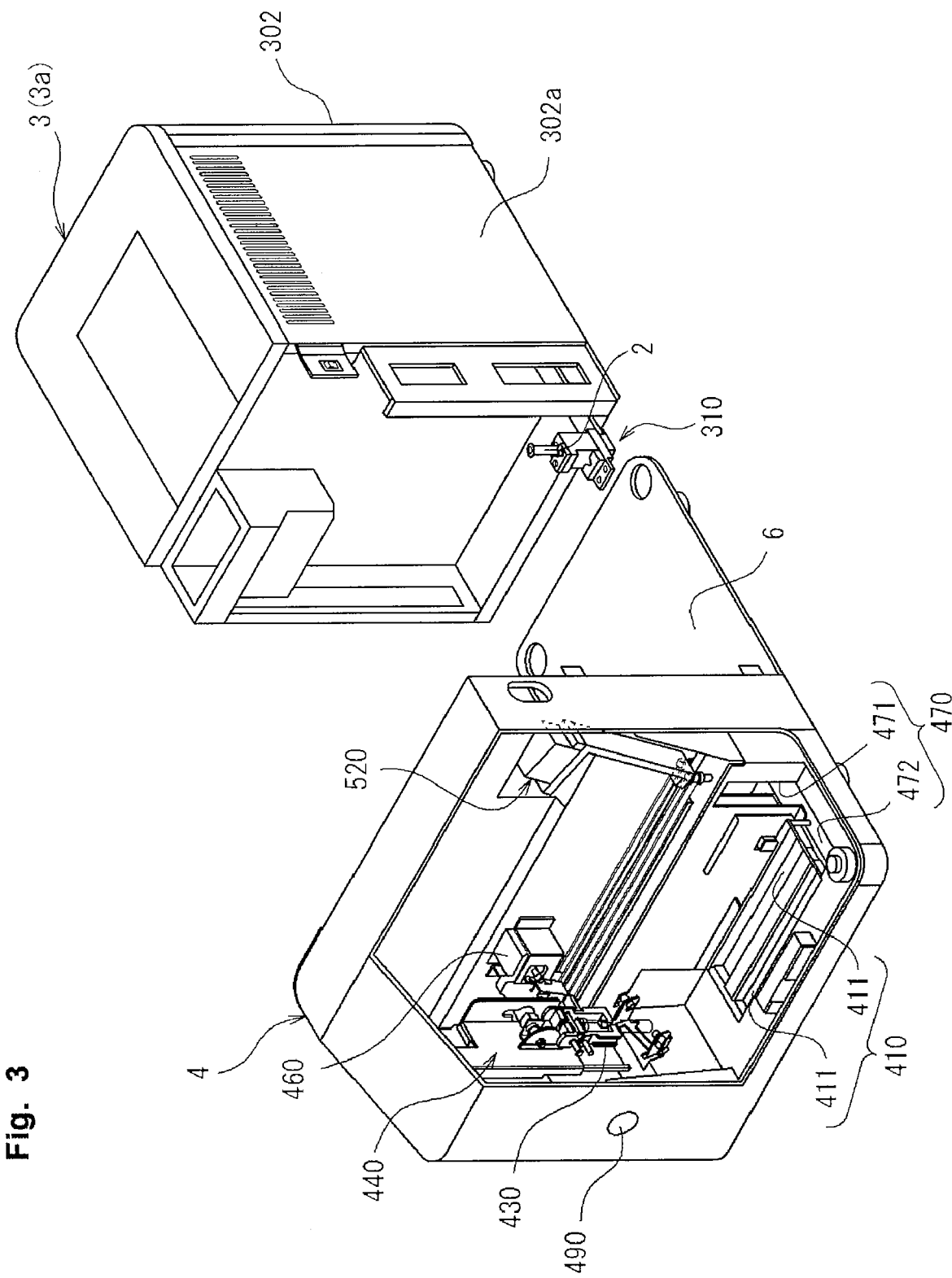
FIG. 3 is an exploded perspective view of a sample analyzer.

The sample analyzer 1 has a sample container supplier 4 subsequently joined to a manual placement-type sample analyzer 3a, as shown in FIG. 3, and the two devices 3a and 4 are integrated so as to be separable, thus configuring a sample analyzer with a detachable sampler attachment. As a result, the sample analyzer 1 not only allows manual placement of sample containers 2, but also automatically supplies sample containers 2.

Moreover, the two devices 3a and 4 may be integrated after initial assembly of the devices during the manufacturing process.

Sample Analyzer Main Body 3 (Manual Placement-type Sample Analyzer 3a)

Figure 4:
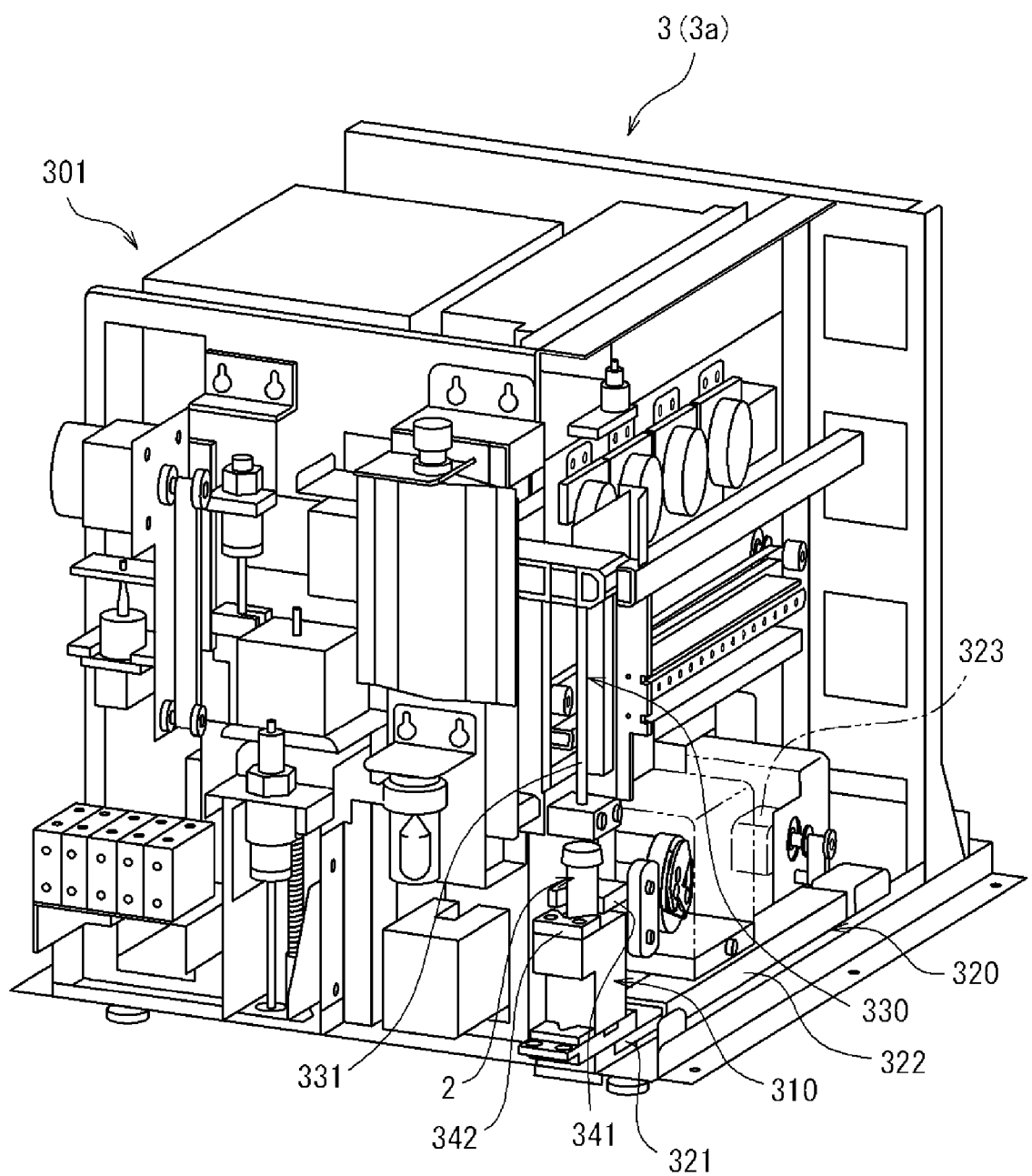
FIG. 4 is a perspective view of the internal mechanism of the manual placement-type sample analyzer.

FIGS. 2 and 4 show the manual placement-type sample analyzer 3a (sample analyzer main body 3). The manual-placement-type sample analyzer 3a is mainly configured by an internal mechanism 301 having a measuring unit for measuring samples and the like, and a casing 302 that houses the internal mechanism unit 301.

The casing 302 is provided with a casing body 302a (refer to FIG. 3) that has an open front (one surface), and a front casing 302b mounted on the casing body 302a so as to obstruct the front opening of the casing body 302a. When the sample container supplier 4 is installed on the sample analyzer main body 3a, the front casing 302b is removed (refer to FIG. 3).

An opening 304 is formed in the bottom right area of the front casing 302b, such that a sample container acceptor 310, in which a sample container 2 is manually set, can move forward from inside the casing 302 to the front of the casing 302 (refer to FIG. 2).

The internal mechanism 301 is provided with a sample container acceptor 310 and a mover 320 that moves the sample container acceptor 310.

The sample container acceptor 310 is provided with a mounting base 312 that has a holding orifice 311 (refer to FIG. 6) for holding a tube-like sample container collection tube in an upright and approximately vertical state. The holding orifice 311 is open at the top, and the hole extends vertically (perpendicular direction). Therefore, setting and replacing a sample container 2 on the sample container acceptor 310 is accomplished by setting and removing the sample container 2 in a vertical direction (perpendicular direction).

Moreover, the holding orifice 311 has a relatively large diameter to allow the insertion of sample containers of various tube diameters.

Figure 5:
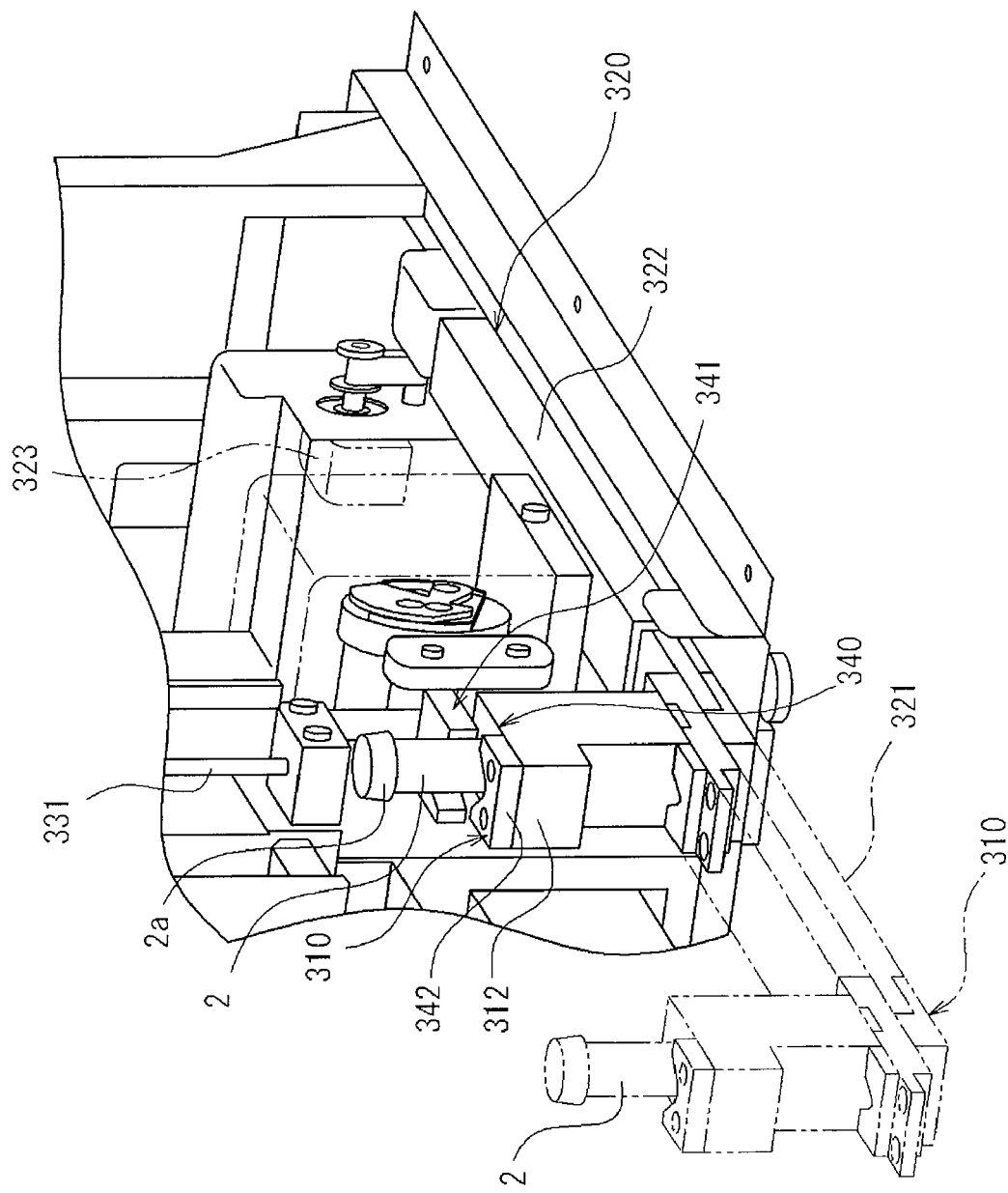
FIG. 5 is an enlargement of the sample container acceptor moving unit of the manual placement-type sample analyzer.

The mover 320 is configured so as to move the mounting base 312 in front-to-back directions. As shown in FIG. 5, the mover 320 is provided with a slider 321 that is movable in forward and backward directions and on the leading end of which is mounted the mounting base 312, a guide 322 that guides the forward and backward movement of the slider 321, and a motor 323 that functions as the drive unit that drives the slider 321.

When the motor 323 rotates, the rotational movement is transmitted to the guide 322 side via a belt 324. This rotational movement is converted to a linear movement by a rotation-to-linear movement conversion mechanism not shown in the drawing that is built into the guide 322, such that the slider 321 is moved in forward and backward directions.

Moreover, since the slider 321 is provided so as to move horizontally, a sample container 2 set in an approximately vertical state on the sample receiver 320 can be moved horizontally while maintaining the vertical condition of the sample container.

When the slider 321 is moved forward, the sample container acceptor 310 projects forward from the opening 304, as shown in FIG. 2, such that a sample container 2 can be set in the holding orifice 311. Furthermore, the position of the sample container acceptor 310 shown in FIG. 2 is referred to as the manual sample container receiving position. When the slider 321 is moved backward, the sample container acceptor 310 is housed within the apparatus, as shown in FIG. 4.

A cover 324 used to close the opening 304 is rotatably provided on the end of the slider 321 (refer to FIG. 2). A spring not shown in the drawing exerts a force so as to incline the cover 324 to the outer side at a predetermined angle. When the slider 321 is retracted, the cover 324 is moved from the state shown in FIG. 2 in an upward direction to close the opening 304, and when the slider 321 advances, the cover 324 is moved forward and downward to the state shown in FIG. 2.

A measurement start button 305 is provided on the front of the casing 302. When the start button 305 is pressed after the sample container 2 has been inserted in the holding orifice 311 of the mounting base 312, the slider 321 is retracted, and the sample container 2 (sample receiver 310) is positioned at the aspirating position (the position shown in FIG. 4) within the apparatus 3. Thus, in the manual placement-type sample analyzer 3a, the sample container acceptor 310 moves between the manual sample container receiving position and the aspirating position.

An aspirator 330 is provided within the apparatus 3 to aspirate the sample within the sample container 2 that is disposed at the aspirating position. The aspirator 330 is provided with an aspiration tube 331 that is moved downward (vertically downward direction) and pierces the stopper 2a that seals the sample container 2, then aspirates the sample within the sample container. The aspirator 330 is further provided with a horizontal drive mechanism for moving the aspiration tube 331 horizontally within the apparatus 3, and a vertical drive mechanism for moving the aspiration tube 331 vertically.

The holding orifice 311 of the sample container acceptor 310 is formed relatively large so as to allow the insertion of sample containers of various diameters as previously mentioned. Therefore, there is a possibility that the sample container 2 accommodated in the holding orifice 311 may be somewhat inclined and eccentrically positioned and leaning within the holding orifice 311. There is concern that the inclination, eccentricity and leaning of the sample container may hinder the aspiration tube 331 as it advances within the sample container 2.

In the present embodiment, a positioning part 340 is provided to position the sample container 2 so as to prevent the sample container from leaning at the aspirating position.

Figure 6:
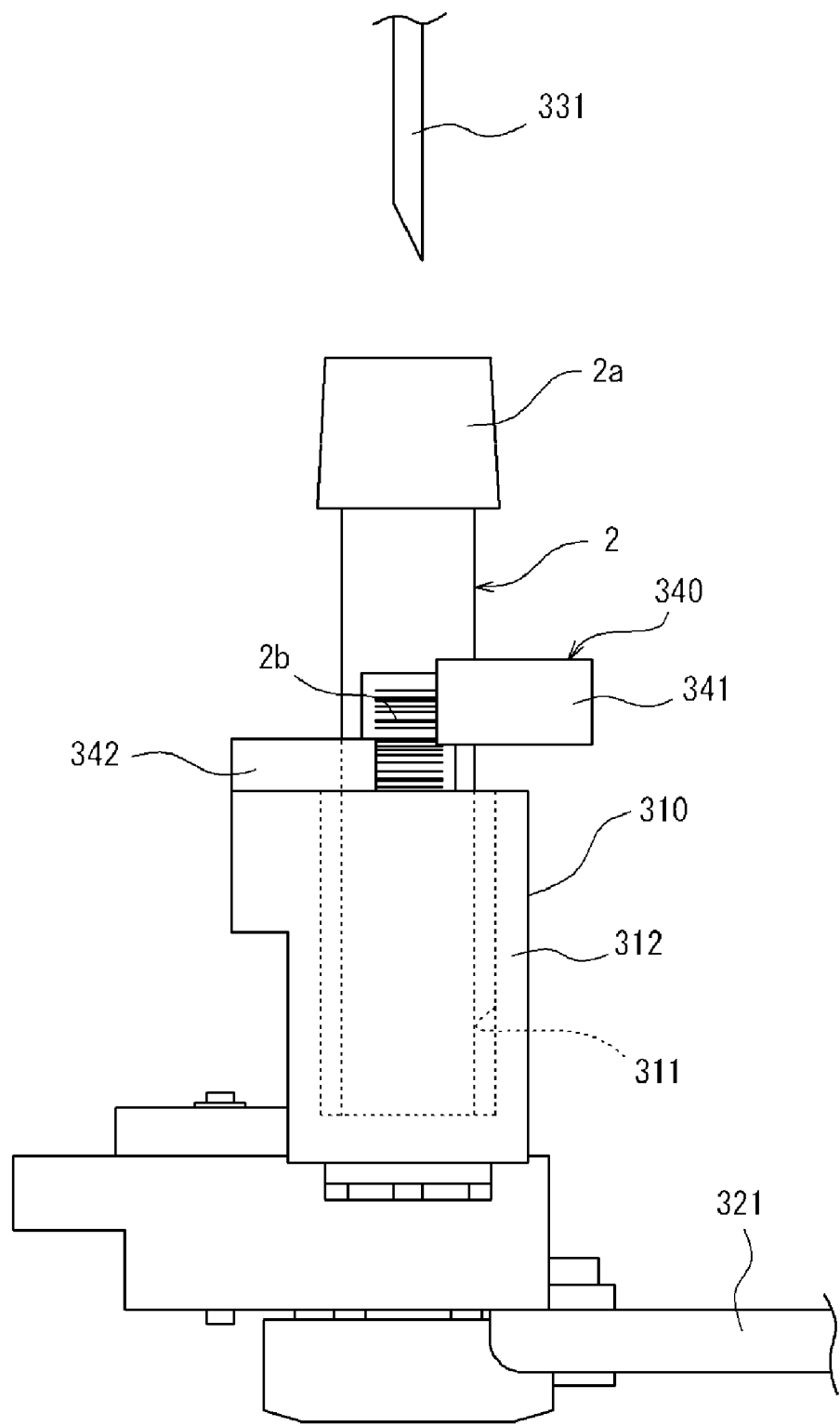
FIG. 6 is a side view of the sample container positioner.

As shown in FIGS. 5 and 6, the positioning part 340 is configured by a stationary positioner 341 provided at a fixed position within the apparatus 3, and a movable positioner 342 provided on the sample container acceptor 310 side, so as to fix the position of a sample container by holding the sample container 2 between both positioners 341 and 342.

The movable positioner 342 is provided at the top of the mounting base 312, and abuts the front side of a sample container 2 inserted in the holding orifice 311. When the sample container acceptor 310 is retracted to the aspirating position, the back side of the sample container 2 abuts the stationary positioner 341, and the sample container 2 is gripped from the front and back by the stationary positioner 341 and the movable positioner 342. Thus, the sample container 2 is held stable and stationary, and ensures reliable aspiration of the sample.

Figure 7:
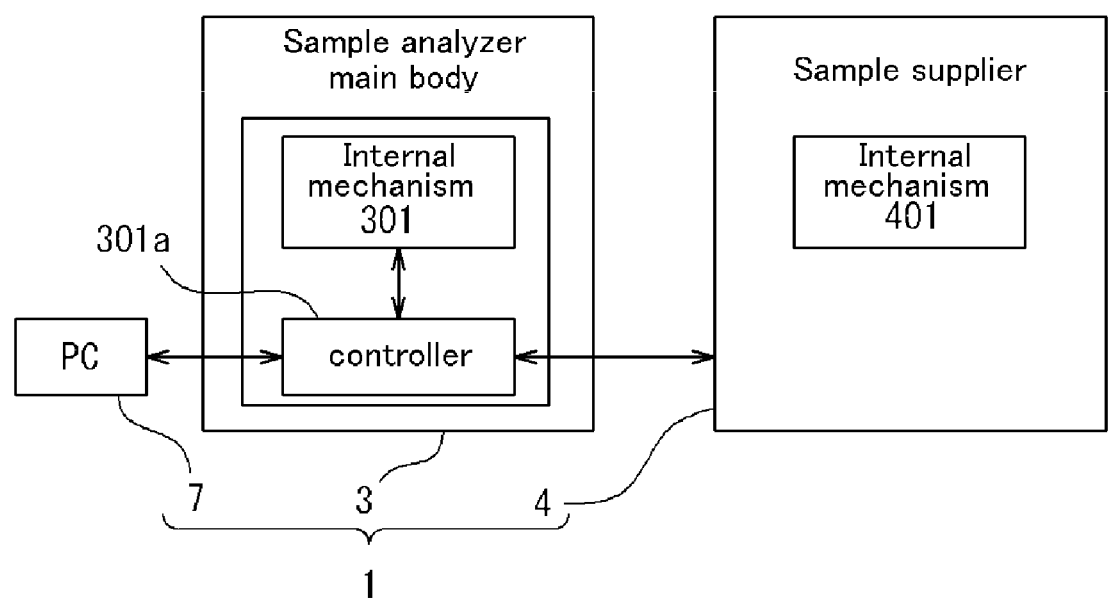
FIG. 7 is a function block diagram of the sample analyzer.

The sample (the blood sample) aspirated by the aspirator 330 is mixed with reagent and transported to the measuring unit. For this measuring process, the internal mechanism 301 of the apparatus 3 is provided with a measurement sample preparing unit configured by a reagent containers containing reagent, reagent supply pump, reagent supply path, and mixing chamber for mixing the sample and reagent, and further provided with a controller 301a for controlling the mechanism 301, and a measuring unit for performing measurements related to red blood cells, white blood cells and platelets in the sample prepared by the measurement sample preparing unit (refer to FIG. 7).

Furthermore, the controller is connected to a computer 7 that performs analysis processing of the measurement results, operations of the apparatus and the like, sends measurement result data to the computer, and receives operation instructions from the computer 7.

When the sample container supplier 4 is installed in the apparatus 3, the controller 301a controls the sample container supplier 4.

Sample Container Supplier (Agitating Apparatus) 4

Figure 8:
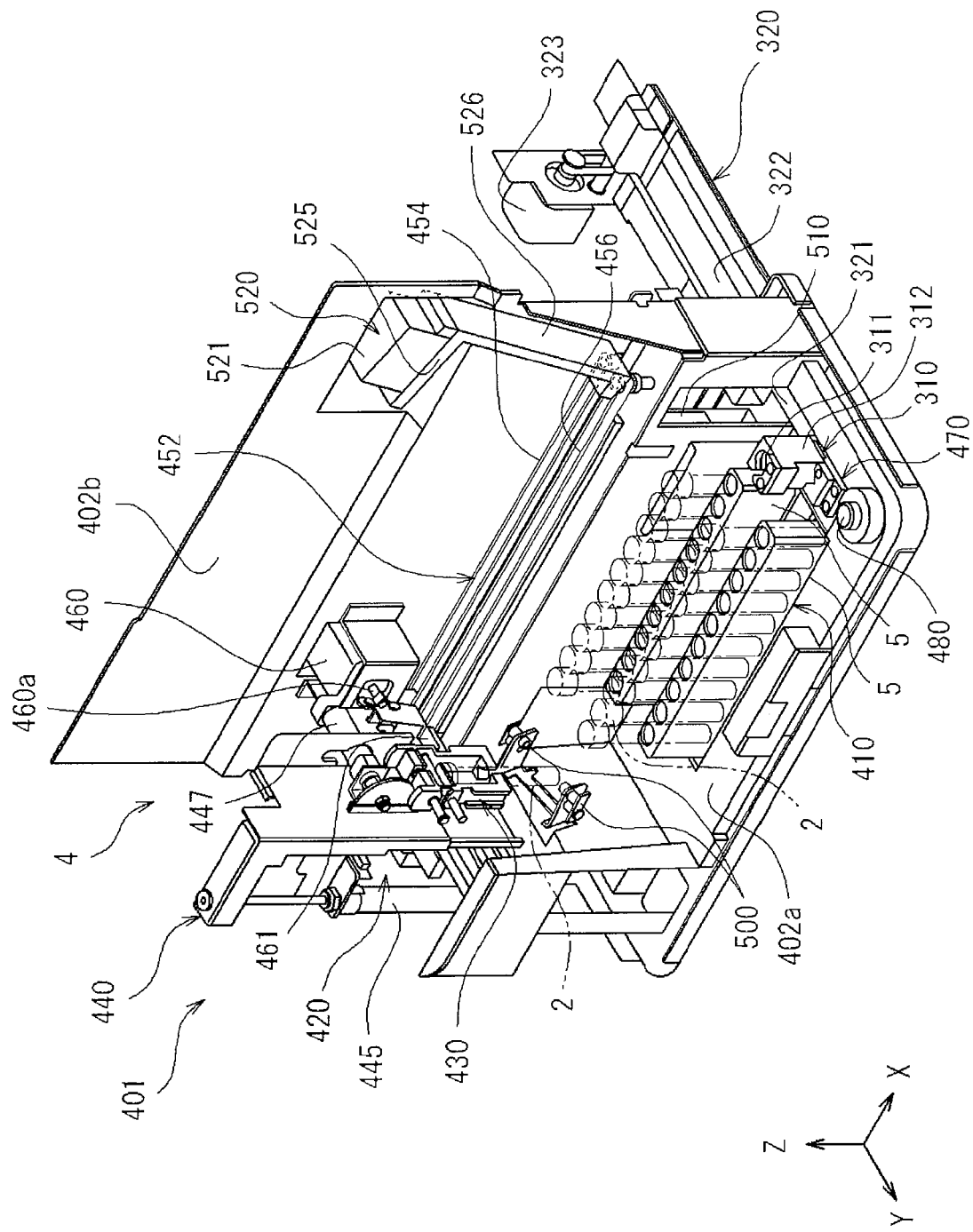
FIG. 8 is a perspective view of the internal mechanism of the sample container supplier.

When a rack 5 holding a plurality of sample containers 2 is set, the sample container supplier 4 shows in FIGS. 1, 3, and 8 automatically removes one sample container 2 from the rack 5, agitates the sample container 2, and supplies the agitated sample container 2 to the sample analyzer 3.

The sample container supplier 4, which functions as an agitating apparatus, is provided with an internal mechanism 401 for agitating and supplying a sample container, and a casing 402 as an apparatus base within which the internal mechanism 401 is installed. FIG. 8 shows the bottom surface 402a and rear surface 402b of the casing 402 that remain when the casing 402 has been removed. FIG. 8 also shows the sample container sample container acceptor 310 and moving part 320 of the sample analyzer main body 3 to facilitate understanding.

As shown in FIG. 3, when the sample container supplier 4 is installed in the manual placement-type sample analyzer 3a (sample analyzer main body 3), the front casing 302b of the apparatus 3 is removed and the sample container supplier 4 is inserted in the front (one side) of the apparatus 3. Furthermore, a mounting plate 6 spans bottom surfaces of both the apparatuses 3 and 4 and is affixed to each by screw or the like, such that both apparatuses 3 and 4 are rigidly coupled.

When the apparatuses 3 and 4 are combined, connective wiring and tubing are required between the apparatuses 3 and 4. For example, the apparatuses 3 and 4 are connected by a power cable for supplying electric power to the electric motor provided in the sample container supplier 4, control signal line allowing the same electric motor to be controlled by the controller 301a of the apparatus 3, air tube for supplying air to the air cylinder provided in the apparatus 4, sensor signal lines for transmitting signals from sensors provided in the apparatus 4 to the controller 301a of the apparatus 3 and the like.

Furthermore, the controller 301a of the apparatus 3 is switchable from a setting for controlling the operation in the manual mode by the apparatus 3, to a setting to control the operation in both the manual mode and the automatic mode.

Rack Holder 410

The bottom surface 402a of the casing (apparatus base) 402 is provided with the rack holder 410 in which the rack 5 is set. The rack holder 410 is capable of holding two (multiple) racks 5 equally spaced in front and back. More specifically, arranged on the casing bottom surface 402a of the rack holder 410 are concavities 411 whose lengths extend laterally and are disposed at equal spacing at front and back. A rack sensor (not shown in the drawing) for detecting the presence of the rack 5 in the rack holder 410 is provided on the casing 402, such that automatic operation for supplying a sample container cannot be performed when a rack 5 is not disposed in the rack holder 410.

An opening 403 is formed on the front surface, right side surface and top surface of the casing 402. Furthermore, an openable cover 404 is mounted on the casing 402 to open and close the opening 403. As shown in FIG. 1, when the cover 404 is open, it is possible to set the rack 5 in the rack holder 410 within the casing 402.

Moreover, although the cover 404 is closed during the sample container automatic supplying operation, the cover 404 is formed of a transparent or semi transparent material to allow visual monitoring of the interior through the cover 404.

Sample Container Supplying Unit 420

The sample container supplier 4 is provided with a sample container supplying unit 420 as one mechanism configuring the internal mechanism 401, and which removes the sample container 2 from the rack 5 in the rack holder 410, agitates the sample container 2, and moves the sample container 2 to the sample analyzer main body 3 side.

The sample container supplying unit 420 is provided with a movable base 440 (refer to FIG. 9) having a hand-like holder 430 for holding the sample container 2, and a moving unit 450 (refer to FIG. 10) that moves the movable base 440 within the apparatus casing (apparatus base) 402.

Moving Base 440

Figure 9:
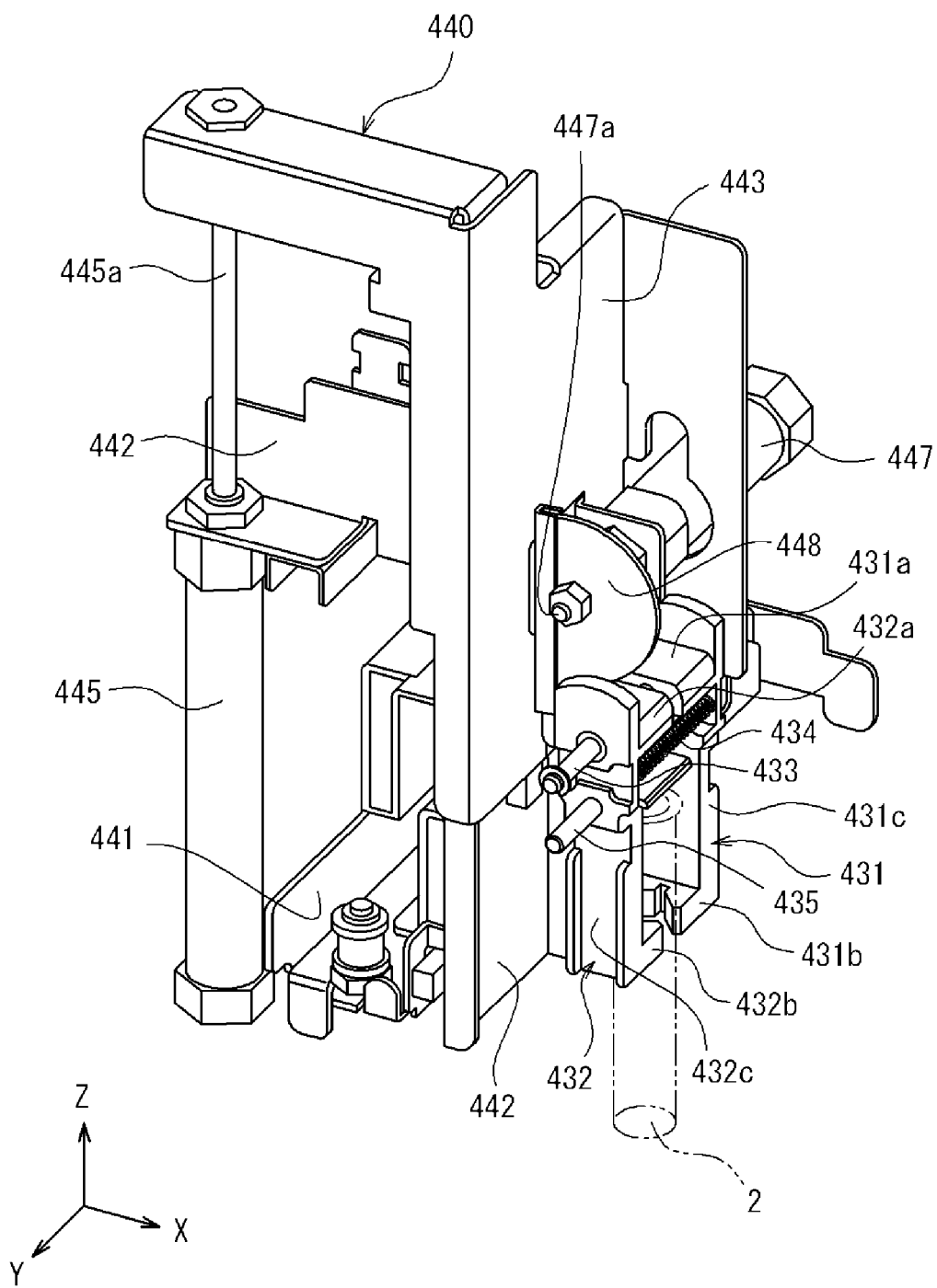
FIG. 9 is a perspective view of the movable base.

As shown in FIG. 9, the moving base 440 is provided with a base body 441, a forward-and-back moving base 442 that is movable in forward-and-backward directions (Y direction in FIG. 9) relative to the base body 441, and an elevator base 443 that is movable in vertical directions (Z direction in FIG. 9) relative to the forward-and-back movable base 442. The elevator base 443 is movable in forward-and-back and vertical directions as viewed from the base body 441.

Furthermore, the holder 430 is mounted on the elevator base 443.

An elevator drive unit (elevator cylinder) 445 that configures the elevator is mounted on the forward-and-back movable base 442. The elevator base 443 is mounted on the leading end of a rod 445a of the elevator cylinder 445. Thus, the elevator base 443 and holder 430 can be raised and lowered relative to the forward-and-back movable base 442 via the extension and retraction of the elevator cylinder 445.

Moving Unit 450

The moving unit 450 moves the holder 430 installed on the moving base 440 within the casing (apparatus base) 402. More specifically, the moving unit 450 moves the movable base 440 laterally (X direction in FIG. 10), and moves the forward-and-back movable base 442 of the movable base in the forward-and-back directions (Y direction in FIG. 10) relative to the base body 441.

Figure 10:
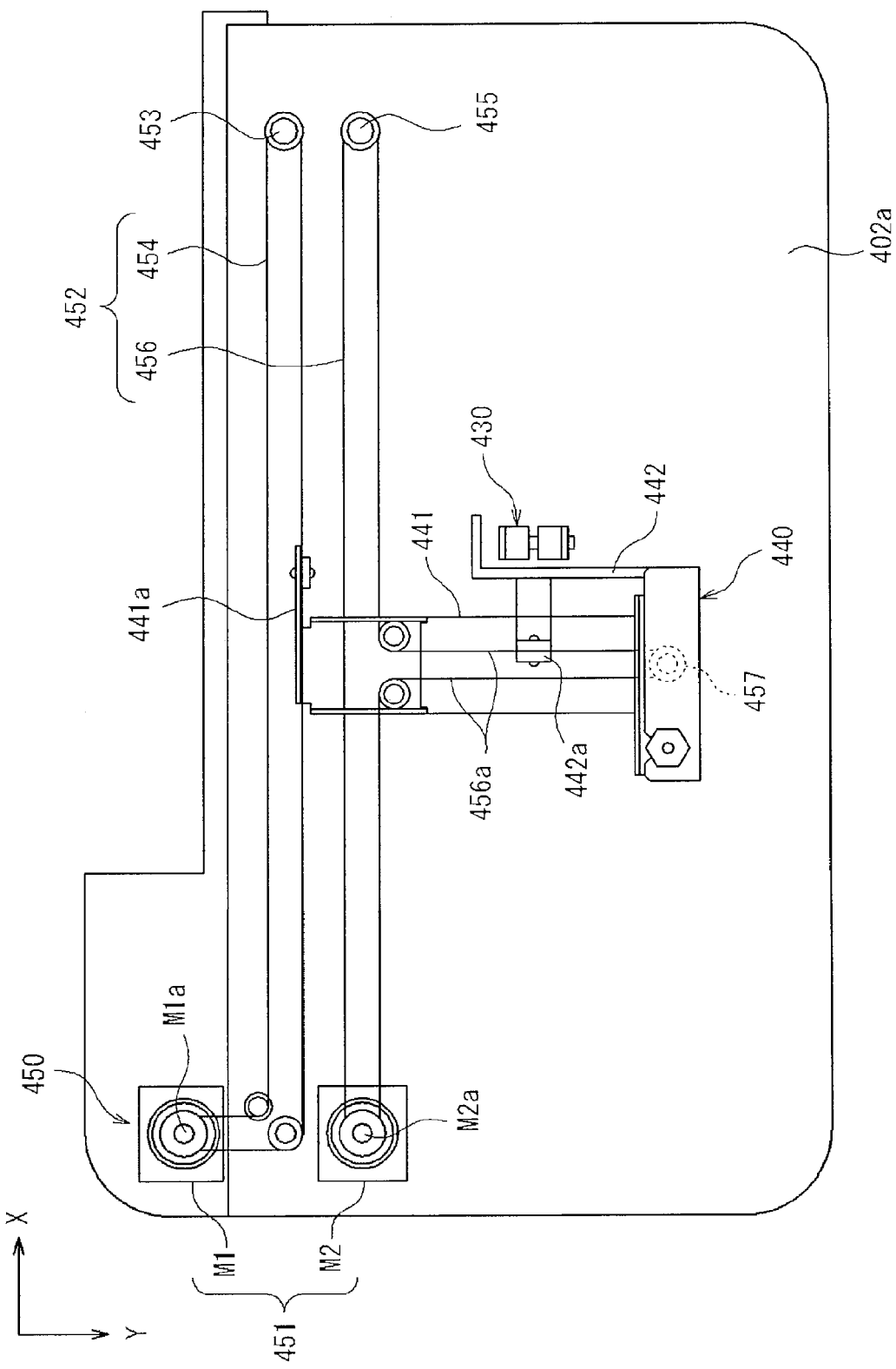
FIG. 10 is a top view of the moving unit of the sample container supplier.

As shown in FIG. 10, the moving unit 450 is provided with a movement drive unit 451 configured by electric motors M1 and M2, and a transmission mechanism 452 for transmitting the drive force of the movement drive unit to the movable base 440 side.

The first motor M1 of the movement drive unit 451 is disposed on the left side of the interior of the casing 402 of the sample container supplier.

A first belt 454 configuring the transmission mechanism 452 is looped between a rotating shaft M1a of the first motor M1 and a first pulley 453 disposed on the right side of the interior of the casing 402 of the sample container supplier. The first belt 454 extends in a lateral direction at a position at the rear of the interior of the casing 402 of the sample container supplier.

Moreover, the second motor M2 of the movement drive unit 452 is disposed to the front of the first motor M1 and at the left side of the interior of the casing 402 of the sample container supplier. A second belt 456 configuring the transmission mechanism 452 is looped between a rotating shaft M2a of the second motor M2 and a second pulley 455 disposed on the right side of the interior of the casing 402 of the sample container supplier. The second belt 456 also extends in a lateral direction at a position on the front side of the first belt 454 and positioned at the rear of the interior of the casing 402 of the sample container supplier. Furthermore, the second belt 456 is also looped around a third pulley 457 provided on the base body 441 of the moving base 440, and has a part 456a that extends in the front-to-back direction so as to form an T-shape overall.

The base body 441 of the movable base 440 is mounted via a mounting stay 441a on a part extending at the front side of the first belt 454, such that when the first belt 454 is moved laterally via the rotation of the first motor M1, the base body 441 is pulled and the entire movable base 440 is moved laterally.

Furthermore, when the movable base 440 is moved laterally, the second motor M2 also rotates to move the front-to-back movable base 442 forward and back.

The front-to-back movable base 442 of the movable base 440 is mounted via a mounting stay 442a on the right side of the front-to-back extension 456a of the second belt 456, such that the front-to-back movable base 442 is moved in front-to-back directions relative to the base body 441 when the second motor M2 is rotated while the rotation of the first motor M1 is stopped.

According to this configuration, the holder 430 provided on the movable base 440 is movable in lateral directions (X direction) front-to-back directions (Y direction), and vertical directions (Z direction) within the apparatus casing 402. That is, the holder 430 can be moved in three-dimensional directions (XYZ directions) via the holder moving mechanisms included in the moving unit 450 and elevator drive unit 445.

Holder 430

Figure 11:
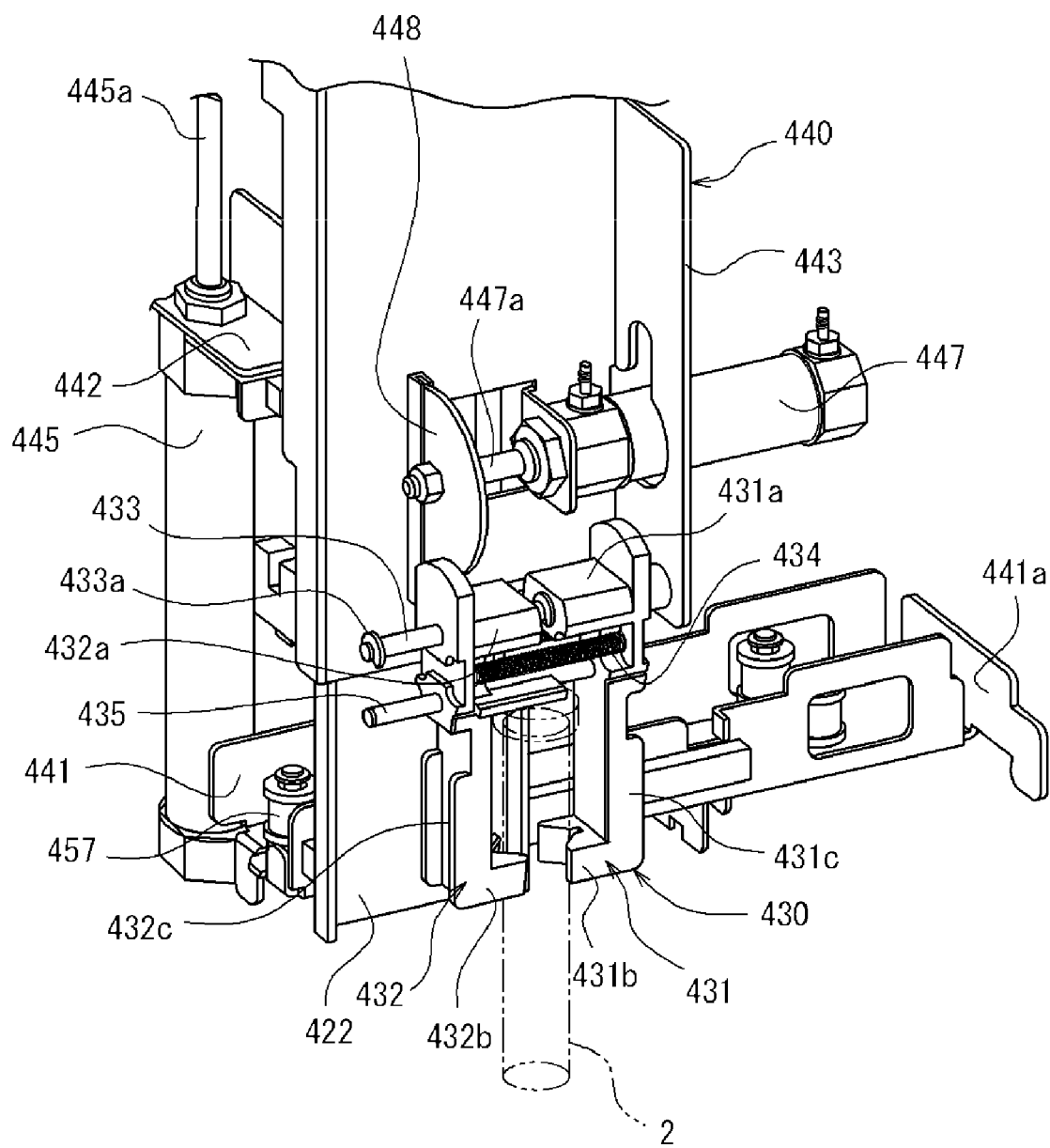
FIG. 11 is a perspective view showing the container holder in the closed condition.
Figure 12:
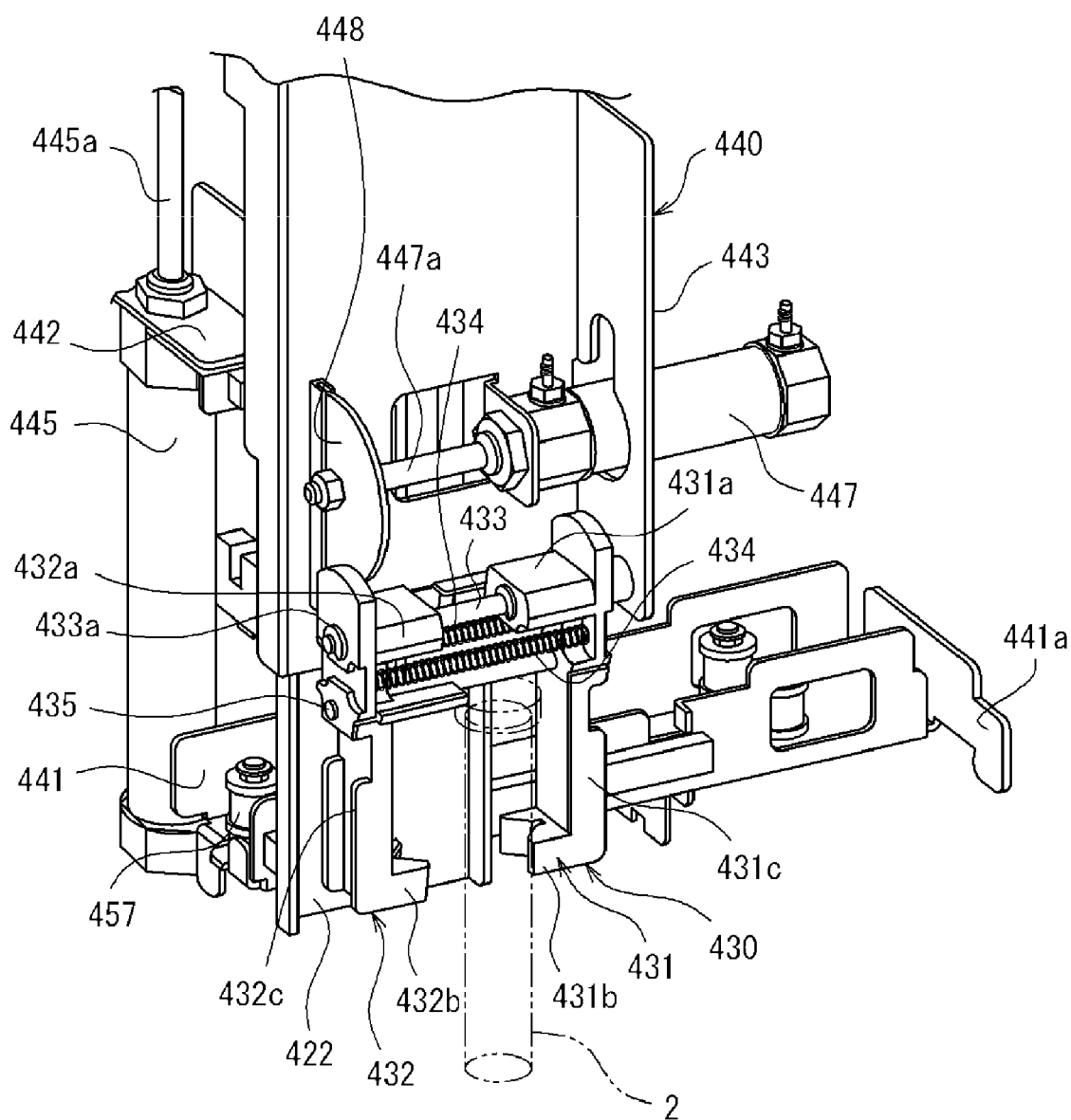
FIG. 12 is a perspective view showing the container holder in the open condition.

As shown in FIGS. 11 and 12, the holder 430 provided on the movable base 440 (elevator base 443) is configured by a pair of finger-like grabbers 431 and 432 that can open and close and has an overall hand-like configuration.

The grabbers 431 and 432 are provided so as to be rotatable on a shaft 433 provided on the elevator base 443. The holder 430 is capable of performing an agitation operation, which is described later, by means of the grabbers 431 and 432 provided so as to be integratedly rotatable on the shaft 433.

The grabbers 431 and 432 are provided with bases 431a and 432a that have holes through which the shaft 433 is inserted, and grabber bodies 431c and 432c that have grippers 431b and 432b extending from the bases 431a and 432a and grip the sample containers 2 by the ends thereof.

The grabber (fixed side grabber) 431 among the two grabbers is prevented from moving in the axial direction of the shaft 433. Furthermore, the other grabber (movable side grabber) 432 is provided so as to be movable in the axial direction of the shaft 433.

A spring 434 is provided between the grabbers 431 and 432, and this spring exerts a force so as to force the movable grabber 432 to make contact with the fixed grabber 431. That is, the grabbers 431 and 432 of the holder 430 are normally closed.

A shaft 435 also is inserted through the grabber bodies 431c and 432c of the grabbers 431 and 432 so as to guide the movement (opening and closing movement) of the movable grabber 432.

Holder Grip Drive Unit 447

A holder grip drive unit (holder operating cylinder) 447 configured by an air cylinder is provided on the elevator base 443 of the movable base 440 to open the holder 430, that is to move the movable grabber 432 relative to the fixed grabber 431. A press plate 448 is mounted on the leading end of a rod 447a of the holder opening/closing cylinder 447 to move the movable grabber 432.

As shown in FIG. 11, when the rod 447a of the holder operating cylinder 447 is extended, the movable side grabber 432 is positioned on the fixed grabber 432 side by the spring 434, such that the holder 430 is closed. When the rod 447a is contracted and the holder 430 is closed, the press plate 448 is separated from the movable grabber 432.

As shown in FIG. 12, when the rod 447a of the holder operating cylinder 447 is extended, the press plate 448 presses the base 432a side of the movable grabber 432, the movable grabber 432 is moved along the shafts 433 and 435, and the holder opens. Thus, a condition 9 is obtained in which the sample container 2 is gripped.

In this condition, the sample container 2 is positioned between the grippers 43 lb and 432b, and when the rod 447a of the holder operating cylinder 447 is contracted as shown in FIG. 11, the press plate 448 separates from the movable grabber 432, and the movable grabber 432 is moved back by the spring 434. Thus, the holder 430 closes, and the sample container 2 can be gripped by the holder 430.

When the press plate 448 presses the movable grabber 432 and the holder 430 is open, the rotation of the grabbers 431 and 432 around the shaft 433 is regulated by contact friction between the press plate 448 and the movable grabber 432 (an operating regulating condition). When the press plate 448 presses the movable grabber 432 and the holder 430 is open, the rotation of the movable grabber 432 is regulated by pinching between a diameter expansion part 433a mounted on the end of the movable grabber 432 and the press plate 448. According to this pinching, the whole of the holder 430 is regulated.

When the holder 430 is closed, however, the press plate 448 and the diameter expansion part 433a separate from the movable grabber 442, and the rotation regulation of the grabbers 431 and 432 by the press plate 448 is released (an operating free condition).

Thus, the press plate 448 and the diameter expansion part 433a function as the regulating part by regulating the rotation when the holder 430 is open and by releasing the regulating rotation when the holder 430 is closed.

Mixing Drive Unit 460

Figure 13:
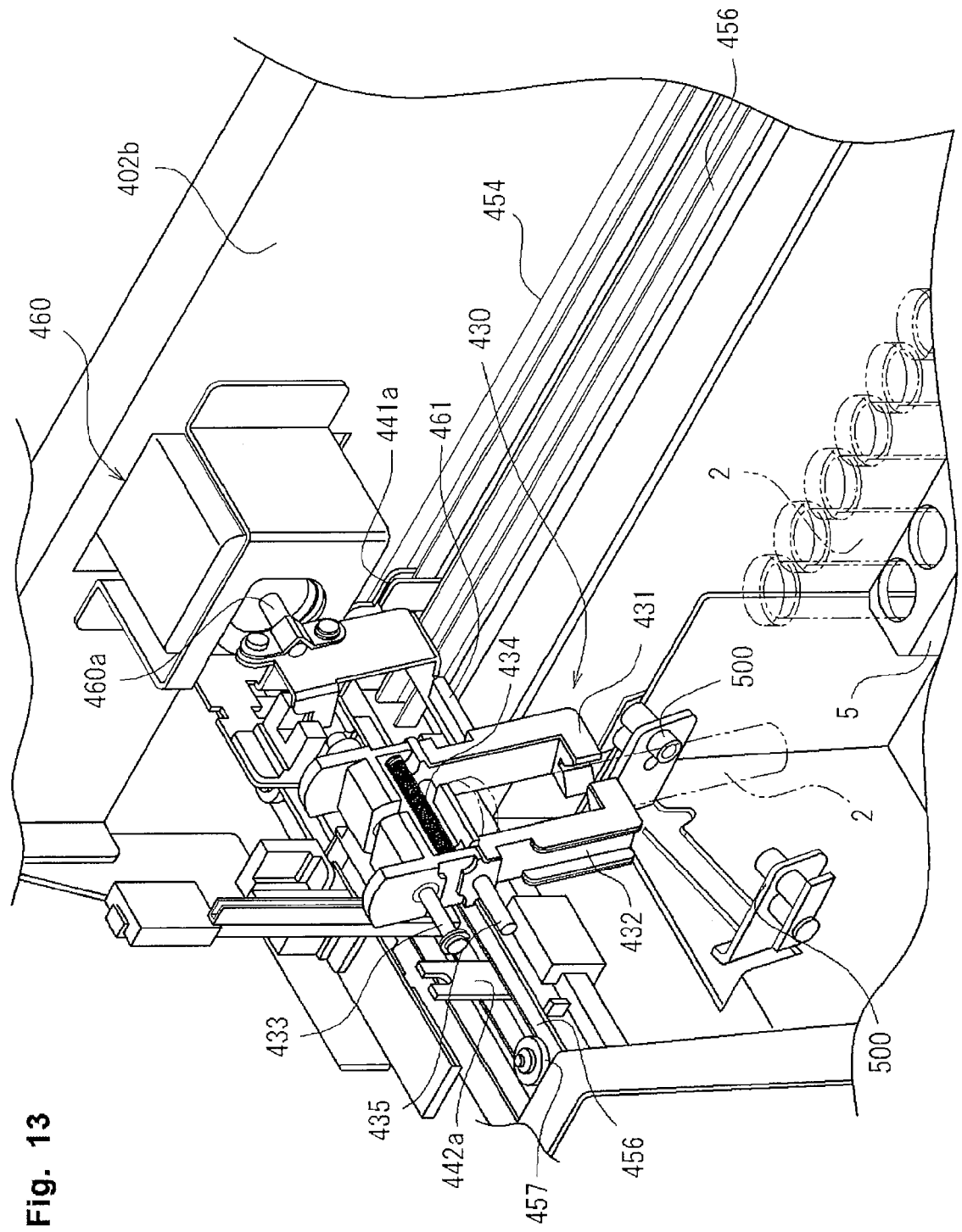
FIG. 13 is a perspective view showing the container holder agitation operation.

As shown in FIG. 13, a mixing drive unit 460 is provided as an internal mechanism 401 of the apparatus 4 to generate a mixing drive force to mix a sample within the sample container 2 before the sample container 2 is supplied to the sample analyzer main body 3.

The mixing drive unit 460 is configured by an electric motor, and the mixing drive unit 460 is fixedly provided at a position on one side (left side) of the rack holder 410 on the rear surface of the casing 402.

Te sides (left side) of the rack holder 410 provided with the mixing drive unit 460 is near the retracted position (movement start position) of the movable base 440 (holder 430).

A contact member 461 is mounted on the rotating shaft 460a of the motor 460 to contact the holder 430 (fixed grabber 431) and transmit the agitation drive force to the holder 430.

Figure 14:
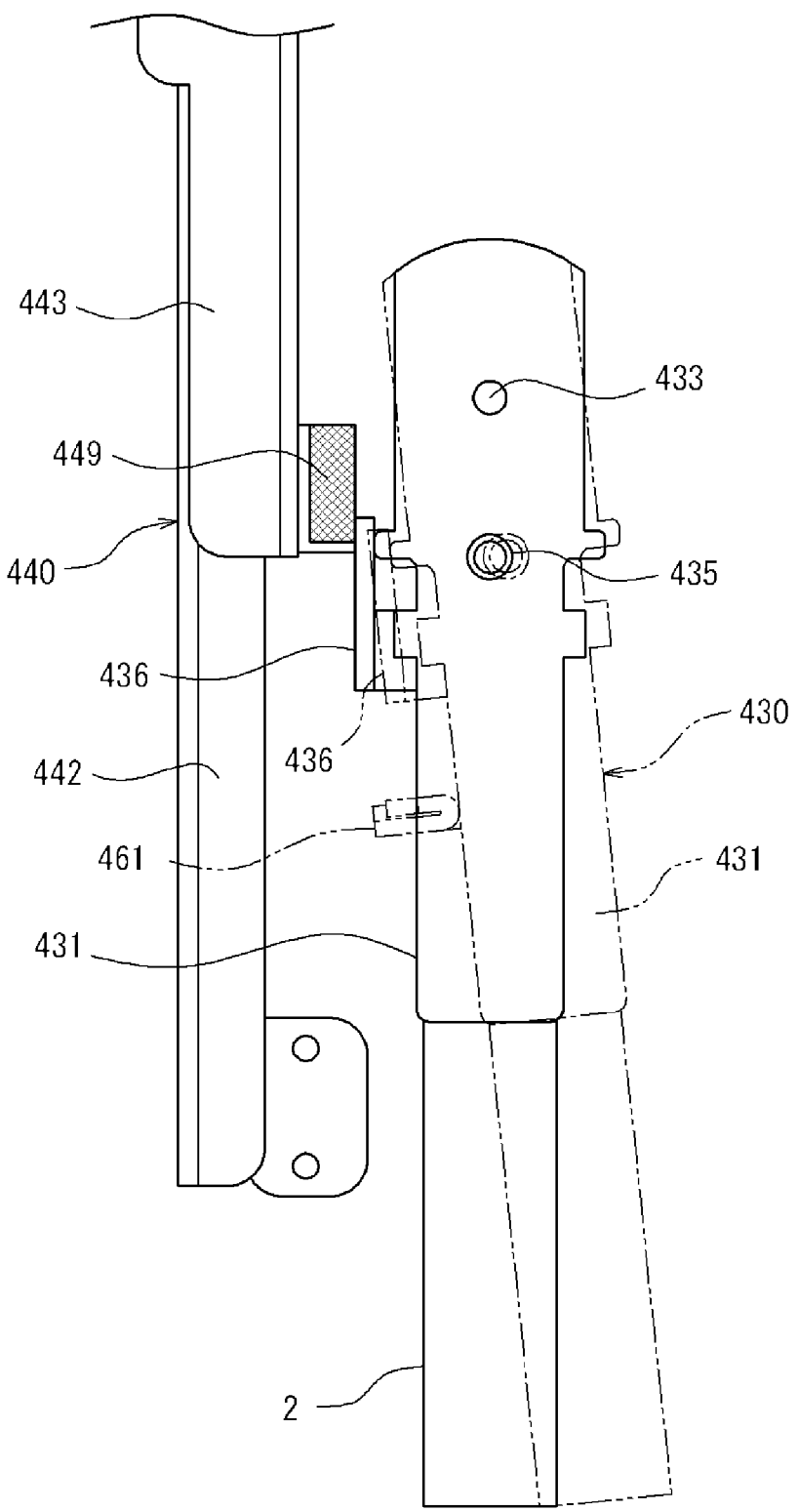
FIG. 14 is a side view showing the regulating state in which the container holder is fixed non-rotatably to the apparatus base, and the state in which the regulation is released via contact with the contact member.

As indicated by the solid line in FIG. 14, the holder 430 normally (when set at the retracted position) hangs downward from the shaft 433 via its own weight.

The holder 430 is attracted by a permanent magnet 449 provided on the elevator base 443 (movable base 440) via metal shard (magnetic body) provided on the fixed grabber 431 of the holder 430 such that the holder 430 does not rotate around the shaft 433 at the hanging position.

When the movable base 440 returns to the retracted position via the moving unit 450, the contact member 461 of the agitation drive unit 460 contacts the holder 430 as it hangs. When the contact member 461 comes into contact with the holder 430 through the movement of the movable base 440, the holder 430 rotates slightly on the shaft 433 as indicated by the dashed line in FIG. 14, such that the metal shard 436 and magnet 449 are released from the magnetic attraction condition.

Thus, the metal shard 436 and the magnet 449 regulate the rotation of the holder 430 about the shaft 433 and function as a regulating part for locking the holder 430 to the movable base 440 side; when the holder is at the retracted position, this regulation is released, and the holder 430 separates from the movable base 440 so as to freely rotate about the shaft 433.

In the present embodiment, when the holder 430 is at the position other than the retracted position (the position above the rack holder 410 or the sample container acceptor 310), the rotation (the mixing operation) of the holder 430 is regulated by the regulation part comprising the metal shard 436 and the magnet 449. When the holder 430 is open, the rotation (the mixing operation) of the holder 430 is regulated by the regulation part comprising the press plate 448 and the diameter expansion part 433a.

When the holder 430 removes the container from the rack 5 of the rack holder 410, returns the container 2 to the rack 5 of the rack holder, sets the container 2 to the sample container acceptor 310 and remove the container from the sample container acceptor 310, it is prevented that the holder 430 freely moves along the pathway of the mixing operation.

The regulation or releasing is operated with the moving of the holder 430 and the opening/closing of the holder 430. The apparatus is simple so as not to need the specific driving part to regulate or release the regulation.

When the holder 430 attains the retracted position and is in a rotatable (agitation operation) state and the motor 460 of the agitation drive unit 460 rotates in one direction, the contact member 461 raises the holder 430 in a lifting operation, as shown in FIG. 15. As a result, the holder 430 is rotated upward and reaches the upper position. Furthermore, when the motor 460 rotates in the opposite direction and the contact member returns to the original position in a restoring operation, the holder 430 rotates downward under its own weight and returns to the lower position.

The agitation operation is accomplished by repeated forward and reverse rotation of the motor 460, and the repeated raising and lowering of the holder 430 holding the sample container 2. In the agitation operation the raising and lowering of the holder 430 is repeated approximately ten times. Since the agitation operation is performed when the sample container 2 is at the retracted position of the movable base 440 without the rack 5, space is conserved.

During the agitation operation, the contact member 461 and the holder 430 alone need be in contact, such that a connective system is not required between the members 461 and 430. Therefore, the agitation drive force can be received when the holder 430 is simply moved near the agitation drive unit 460, and the agitation drive force can not be received when the holder 430 is moved away from the agitation drive unit 460.

Receiver Unit 470 of the Sample Container Acceptor 310

As shown in FIGS. 1 and 3, a receiving unit 470 is provided on the casing 402 of the sample container supplier to receive the arriving sample container acceptor 310 of the sample analyzer main body 3. The receiving unit 470 is provided on the other side (right side) of the rack holder 410 in the lateral direction.

The receiving unit 470 has an opening 471 formed on the bottom right part of the rear surface 402b of the casing 402, and a concavity 472 that accommodates the sample container acceptor 310 that has moved forward and passed through the opening 471 from the sample analyzer main body 3.

The sample container acceptor 310 can advance into the casing 402 of the sample container supplier even when a wall (casing rear surface 402b) separates the sample analyzer main body 3 and the sample supplier 4 via the provision of the opening 471.

Furthermore, the position of the concavity 472 is the position at which the sample container 2 is supplied by the sample supplier 420 (sample container supplying position), and the sample container acceptor 310 can accept the sample container 2 by advancing the sample container acceptor 310 into the concavity 472.

Sample Container 2 Manual Placement Mode (Manual Mode) in the Sample Analyzer 1

The sequence of the manual mode for setting a sample container 2 manually in the sample analyzer 1 having the previously described configuration is described below.

As shown in FIG. 8, a sample container 2 containing a sample manually agitated beforehand is inserted in the holding orifice 11 of the sample acceptor 310 when the sample container acceptor 310 is moved forward from the sample analyzer main body 3 and received by the receiver 470 of the sample container supplier 4. When the manual measurement start button 480 provided on the casing bottom surface 402a of the sample container supplier 4 is pressed, the controller 301a retracts the slider 321. Then, a manually set sample container 2 (sample acceptor 310) is positioned at the aspirating position (position in FIG. 4) within the sample analyzer main body 3.

The sample of the sample container 2 at the aspirating position is aspirated by the aspirator 330, and measured by the measuring unit. Then the measurement results are analyzed by a computer not shown in the drawing.

The manual mode operation, and measurement and analysis processes after placement are basically identical to the sequence in the manually placement mode of the manual placement-type sample analyzer 3a.

In the sample analyzer 1 with the installed sample container supplier 4, the forward extension of the sample container acceptor 310 is greater than the manual placement-type sample analyzer 3a without an installed sample container supplier 4, such that the sample container acceptor 310 can be reliably advanced into the interior of the sample container supplier 4. That is, the sample container supplying position of the sample analyzer 1 is positioned farther forward than the manual sample container setting position in the manual placement-type sample analyzer 3a.

Moreover, the forward extension of the sample container acceptor 310 can be switched by the setting of the controller 301a.

Sample Container 2 Automatic Supplying Operation (Automatic Mode) in Sample Analyzer 1

In the execution of the automatic mode, the rack 5 holding the sample container 2 is set in the rack holder 410, and the cover 404 is closed on the sample container supplier 4, as shown in FIG. 1. he rack 5 holds the sample container 2 in an approximately upright vertical state.

Then, when the automatic measurement start button 490 is pressed, the sample container 2 is automatically supplied and the sample measured. Whether or not the cover 404 is closed is detected by a cover sensor not shown in the drawing; when the cover 404 is not closed, the automatic measurement can not start.

The automatic supply of the sample container 2 is controlled as follows by the controller 301a. First, at the start of the automatic mode, the movable base 440 that has the holder 430 is at the movement start position (retracted position) shown in FIGS. 3 and 8, and the operation starts from this position. The movable base 440 with the holder 430 is moved from the movement start position to the position of the sample container 2 to remove one of the two sample containers 2 in the rack 5 set in the rack holder 410.

When the holder 430 is positioned above the sample container 2 to be removed, the holder 430 is opened and the holder 430 is lowered in this open state. After lowering, the holder 430 is closed and raised while gripping the sample container 2, then returns to the movement start position (mixing position).

The space between the front and rear concavities 441 of the rack holder 410 is set to allow passage of the sample container 2 held by the holder 430. Therefore, when the holder 430 is moved laterally above the rack holder 410 holding the sample container 2, the sample container 2 held by the holder 430 can pass through the space between the sample containers 2 (front and rear space) in the rack 5 set in the front and back concavities 441.

As a result, the holder 430 holding the sample container 2 can be lifted above the rack holder 410 without raising the held sample container 2 to as position higher than the sample container 2 in the rack 5. That is, without raising the holder 430 very much, the holder 430 can be moved above the rack holder 410 while avoiding contact between the held sample container 2 and the sample container 2 in the rack 5.

Thus, the raising height is very slight when moving the holder 430 (movable base 440), such that the operation can be performed quickly and the apparatus can be made more compactly (particularly in the height direction of the apparatus).

Moreover, a sample container sensor 500 is provided to detect whether or not the holder 430 holds a sample container 2 when the holder 430 (movable base 440) holding the sample container 2 returns to the movement start position. If the holder 430 holds a sample container 2, the mixing operation proceeds. When the holder 430 does not hold a sample container 2, the same operation as described above is performed to remove a sample container 2 from the other position of the rack 5.

As shown in FIG. 13, during the mixing operation, the mixing drive unit 460 is rotated to vertically rotate the contact holder 430 to mix the sample within the sample container 2.

When the mixing operation ends, the holder 430 returns to the condition of hanging in a perpendicular direction as shown in FIG. 1.

The mixing position need not to be identical with the retracted position, the mixing position may be near the retracted position.

Then, the holder 430 (movable base 440) holding the sample container 2 holds the sample container 2 in a near vertical state, crosses above the rack holder 410, and moves to a position above the sample container acceptor 310 (receiver 470) astride the rack holder 410.

Then, the holder 430 is lowered, and the sample container 2 is inserted in the sample container receiver 310. Thus, the sample container 2 is set in the sample container receiver 310 in the sample container receiver 310 in a near vertical upright state. Thereafter, the holder 430 opens, separates from the sample container 2, and is lifted.

Then, the slider 321 is retracted and the information recording area (barcode) 2b adhered to the sample container 2 is read by a reading unit (barcode reader) not shown in the drawing, and the sample container 2 (sample acceptor 310) is positioned at the aspirating position (position shown in FIG. 4) within the sample analyzer main body 3.

The sample of the sample container 2 at the aspirating position is aspirated by the aspirator 330, and measured by the measuring unit. Then the measurement results are analyzed by a computer not shown in the drawing.

When the sample has been aspirated from the sample container 2, the slider 321 advances and the sample container acceptor 310 is again positioned at the receiver 470.

The holder 430 is again lowered to collect the aspirated sample container 2, and the sample container 2 in the sample container acceptor 310 is gripped and lifted. Then, the holder 430 moves to the position of the rack 5, and the sample container 2 is returned to the rack 5.

The holder 430 (movable base 440) returns to the movement start position after the aspirated sample container 5 has been returned to the rack 5.

Thereafter, the same automatic supplying measurement and analysis are performed for the other sample container in the rack 5.

The present invention is not limited to the above embodiment and may be variously modified.

What is claimed is:

1. An agitating device for agitating a blood sample in a sample container, comprising:
   a base comprising a horizontally-supported shaft;
   a container holder comprising a first hand and a second hand, the first hand comprising a first hole at one end and a first hold portion at an opposite end, the second hand comprising a second hole at one end and a second hold portion at an opposite end, the first and second holes accommodate the horizontally-supported shaft inserted therethrough, wherein the first and second hands are rotatable about the shaft and the first and second hold portions face each other,
   wherein the first hand is free to slide along the horizontally-supported shaft in an axial direction of the shaft and the second hand is fixed to the horizontally-supported shaft in the axial direction of the shaft; and
   an agitation drive unit comprising a contact member engaging a receptacle in the container holder and a reciprocating drive source coupled to the contact member that rotates the container holder about the horizontally-supported shaft between a vertical position and an inclined position.

2. The agitating device of claim 1, wherein the container holder holds the sample container between the first and second hold portions.

3. The agitating device of claim 1, wherein the container holder further comprises a spring provided between the first and second hands.

4. The agitating device of claim 3, wherein the spring exerts an attractive force between the first hold portion and the second hold portion.

5. The agitating device of claim 4, wherein the container holder further comprises a guide shaft for guiding axial movement of the first hand.

6. The agitating device of claim 5, further comprising a container holder drive unit having an axially extendable plate that engages the first hand and applies an axial force against the first hand that opposes the attractive force of the spring and moves the first hand away from the second hand along the horizontally-supported shaft.

7. The agitating device of claim 6, wherein the container holder drive unit comprises an air cylinder.

8. The agitating device of claim 6, further comprising a restrict member located on the horizontally-supported shaft that presses against the first hand and opposes the axial force exerted by the plate to restrict the rotation of the container holder about the horizontally-supported shaft when the first and second hands are separated.

9. The agitating device of claim 1, further comprising a magnet physically attached to the base, wherein the container holder is magnetically attracted to the base and the contact member exerts a reciprocal force against the container holder that opposes the magnet attraction.

10. The agitating device of claim 1 further comprising an elevator drive unit having an extendable shaft coupled to the base, the extendable shaft applying a reciprocal force against the base to reciprocally move the base in a vertical direction relative to the axial direction of the horizontally-supported shaft.

11. A blood sample analyzer for analyzing a blood sample in a sample container, comprising:
 a base comprising a horizontally-supported shaft;
 a container holder comprising a first hand and a second hand, the first hand comprising a first hole at one end and a first hold portion at an opposite end, the second hand comprising a second hole at one end and a second hold portion at an opposite end, the first and second holes accommodate the horizontally-supported shaft inserted therethrough, wherein the first and second hands are rotatable about the shaft and the first and second hold portions face each other;
 wherein the first hand is free to slide along the shaft in an axial direction of the shaft and the second hand is fixed to the horizontally-supported shaft in the axial direction of the shaft
 an agitation drive unit comprising a contact member engaging a receptacle in the container holder and a reciprocating drive source coupled to the contact member that rotates the container holder about the horizontally-supported shaft between a vertical position and an inclined position;
 an aspirator comprising an aspiration tube and aspirating a blood sample contained in the agitated sample container;
 a measurement sample preparer comprising a chamber for preparing a measurement sample by mixing the aspirated blood sample and a reagent; and
 a measurement part measuring blood cells contained in the measurement sample.

12. The blood sample analyzer of claim 11, wherein the container holder holds the sample container between the first and second hold portions.

13. The blood sample analyzer of claim 11, wherein the container holder further comprises a spring provided between the first and second hands.

14. The blood sample analyzer of claim 11, further comprising a container holder drive unit having an axially extendable plate that engages the first hand and applies an axial force against the first hand that opposes the attractive force of the spring and moves the first hand away from the second hand along the horizontally-supported shaft.

15. The blood sample analyzer of claim 14, further comprising a restrict member located on the horizontally-supported shaft that presses against the first hand and opposes the axial force exerted by the plate to restrict the rotation of the container holder about the horizontally-supported shaft when the first and second hands are separated.

16. The blood sample analyzer of claim 11 further comprising an elevator drive unit having an extendable shaft coupled to the base, the extendable shaft applying a reciprocal force against the base to reciprocally move the base in a vertical direction relative to the axial direction of the horizontally-supported shaft.

17. An agitating device for agitating a blood sample in a sample container, comprising:
 a base comprising a horizontally-supported shaft;
 a container holder comprising a first hand and a second hand, the first hand comprising a first hole at one end and a first hold portion at an opposite end, the second hand comprising a second hole at one end and a second hold portion at an opposite end, the first and second holes accommodating the horizontally-supported shaft inserted therethrough, wherein the first and second hands are rotatable about the shaft and the first and second hold portions face each other and the container holder holds a sample container by sandwiching the sample container between the first and second hold portions, wherein the container holder holding the sample container hangs downward from the shaft and is rotatable about the shaft; and
 an agitation drive unit comprising a contact member for contacting the container holder holding the sample container and a reciprocating drive source coupled to the contact member, wherein the reciprocating drive source reciprocates the contact member that swings the container holder holding the sample container.

18. The agitating device of claim 17, wherein the container holder further comprises a spring provided between the first and second hands.

19. The agitating device of claim 18, wherein the spring exerts an attractive force between the first hold portion and the second hold portion.

20. A blood sample analyzer for analyzing a blood sample in a sample container, comprising:
 a base comprising a horizontally-supported shaft;
 a container holder comprising a first hand and a second hand, the first hand comprising a first hole at one end and a first hold portion at an opposite end, the second hand comprising a second hole at one end and a second hold portion at an opposite end, the first and second holes accommodating the horizontally-supported shaft inserted therethrough, wherein the first and second hands are rotatable about the shaft and the first and second hold portions face each other and the container holder holds a sample container by sandwiching the sample container between the first and second hold portions, wherein the container holder holding the sample container hangs downward from the shaft and is rotatable about the shaft;
 an agitation drive unit comprising a contact member for contacting the container holder holding the sample container and a reciprocating drive source coupled to the contact member, wherein the reciprocating drive source reciprocates the contact member that swings the container holder holding the sample container;
 an aspirator comprising an aspiration tube and aspirating a blood sample contained in the agitated sample container;
 a measurement sample preparer comprising a chamber for preparing a measurement sample by mixing the aspirated blood sample and a reagent; and
 a measurement part measuring blood cells contained in the measurement sample.

* * * * *